United States Patent
Berger (10) Patent No.: US 6,539,311 B1
(45) Date of Patent: Mar. 25, 2003

(54) APPARATUS AND METHOD FOR MEASURING CONCENTRATIONS OF A CHEMICAL/BIOLOGICAL/NUCLEAR AGENT IN AN ENVIRONMENT

(75) Inventor: Eugene L. Berger, San Antonio, TX (US)

(73) Assignee: The Mitre Corporation, McLean, VA (US)

( * ) Notice: Subject to any disclaimer, the term of this patent is extended or adjusted under 35 U.S.C. 154(b) by 152 days.

(21) Appl. No.: 09/698,108

(22) Filed: Oct. 30, 2000

(51) Int. Cl.[7] ............... G06F 15/18; G06F 19/00
(52) U.S. Cl. ............... 702/23; 702/32; 700/52; 706/14
(58) Field of Search ............... 702/19, 22, 23, 702/24, 25, 26, 30, 32; 435/4; 340/600, 603; 250/482.1, 472.1, 484.5; 436/58, 902; 700/52; 706/14

(56) References Cited

U.S. PATENT DOCUMENTS

| | | | | |
|---|---|---|---|---|
| 4,642,463 A | * | 2/1987 | Thoms | 250/336.1 |
| 4,695,730 A | * | 9/1987 | Noda et al. | 250/370.07 |
| 4,896,143 A | * | 1/1990 | Dolnick et al. | 340/634 |
| 4,985,017 A | * | 1/1991 | Theeuwes | 604/82 |
| 5,173,609 A | * | 12/1992 | Lacoste et al. | 250/370.07 |
| 5,218,553 A | * | 6/1993 | de Loos-Vollebregt et al. | 356/326 |
| 5,464,750 A | * | 11/1995 | Sanders et al. | 435/29 |
| 5,469,369 A | * | 11/1995 | Rose-Pehrsson et al. | 340/632 |
| 5,535,135 A | * | 7/1996 | Bush et al. | 123/672 |
| 5,608,655 A | * | 3/1997 | Moughanni et al. | 340/7.1 |
| 5,754,622 A | * | 5/1998 | Hughes | 378/108 |
| 5,764,150 A | * | 6/1998 | Fleury et al. | 340/632 |
| 5,841,142 A | * | 11/1998 | Duftschmid et al. | 250/336.1 |
| 5,969,623 A | * | 10/1999 | Fleury et al. | 340/632 |
| 6,183,950 B1 | * | 2/2001 | Madonna et al. | 435/5 |

OTHER PUBLICATIONS

Skliar et al., "Monitoring and Detection of Indoor Air Contamination", IEEE, Jun. 1997.*

* cited by examiner

*Primary Examiner*—Patrick Assouad
(74) *Attorney, Agent, or Firm*—Rosenberg, Klein & Lee (57) ABSTRACT

An apparatus and method for measuring chemical, biological, nuclear agents in an environment includes several detectors capable of measuring concentrations of the agents in the environment and a processor capable of operating an algorithm which, based on two sequential measures of concentration of the agent, estimates decay or elevation rate of the concentrations of the agent and feeds this estimated change rate to a Kalman filter which predicts the next measurement. The predicted next measurement of concentration is compared with the measured concentration and the error is calculated based on the discrepancy between the measured and predicted concentrations of the agent in the environment. Using this error, the attributes of the Kalman filter are adjusted to lower noise signals and improve further predictions of the concentration of the agent during the mission time.

17 Claims, 8 Drawing Sheets

APPARATUS AND METHOD FOR MEASURING CONCENTRATIONS OF A CHEMICAL/BIOLOGICAL/NUCLEAR AGENT IN AN ENVIRONMENT

FIELD OF THE INVENTION

The present invention relates to a measurement technique; and more particularly to a method and apparatus for measurement of concentrations and accumulated dosages of chemical, nuclear, and biological agents contained in closed environments, such as interiors of aircrafts, buildings, cars, or open environments, such as battlefields, or clouds of hazardous gases moving from place to place, etc.

More in particular, the present invention relates to an apparatus capable of predicting concentrations of vapors at any time during some predetermined mission and the capability of predicting dosages accumulated during the mission time.

Further, the present invention relates to chemical/biological/nuclear detectors in which a Kalman filter, with automatically adjusted filter attributes, is used for low noise prediction of concentrations and accumulated dosages of chemical, biological, nuclear agents, with the purpose of warning/dewarning of people exposed to these agents during a mission time.

Furthermore, the present invention relates to a chemical/biological/nuclear detector where performance is based on an algorithm that accumulatively:

(1) estimates decay (or elevation) rates and amplitude attributes of the chemical/biological vapors in any environment;

(2) estimates chemical/biological vapor dosage accumulated by users in the environment;

(3) predicts the chemical/biological vapor dosage accumulated by the users at the end of a mission;

(4) warns the user when the predicted dosages exceed the myosis level; and (5) dewarns the users when the concentration of the chemical/biological vapor is so low that for the remaining mission time, the dosage levels will be lower than the myosis level.

The present invention also relates to a simulation model of a chemical/biological/nuclear detector which allows evaluation and analysis of a detector's performance requirements, sensitivity and accuracy, algorithms, performance of a dosage monitor and a concentration monitor, automation of a detector warning and dewarning method; and measures detoxication of the chemical/biological/nuclear vapors.

The present invention also is related to warning and dewarning methods which would provide the user with advance information prior to harmful effects becoming apparent thereby reducing the harm associated with the user's exposure to chemical, nuclear, biological agents, while simultaneously decreasing user inconvenience by allowing the user to remove protective gear, such as a mask when such is no longer of necessity during a mission.

BACKGROUND OF THE INVENTION

In general, it is important to know in an environment containing hazardous chemical, nuclear, or biological agents, how the agents change their concentration over a period of time, and what dosage of such agents have accumulated over a certain period of time in living organisms exposed to the hazardous vapors.

Routinely, chemical, biological, nuclear detectors measure the concentrations of the hazardous material in the environment at predetermined periods of time during a mission. With this approach of making measurements of the concentration of the vapors during the duration of the mission, users exposed to the hazardous vapors in the environment do not know in advance when the dosage of accumulated hazardous material will reach harmful levels which may be detrimental to their health. Moreover, based upon prior procedures, users in the environment containing hazardous substances and carrying masks are not given advance information as to when they can remove their masks responsive to relatively low and harmless concentrations of hazardous vapors extrapolatively calculated for the remainder of the mission.

It is not believed that any mechanisms or techniques have been developed which provide for low noise prediction of concentration and accumulated dosage of chemical, biological, or nuclear vapors in a hazardous environment and which further predict when the users are to use protective clothing such as masks in order to avoid harm associated with chemical/biological agents they are exposed to or alternatively to remove such protective clothing when hazardous vapors are predicted to be at a relatively safe level.

SUMMARY OF THE INVENTION

It is an object of the present invention to provide an apparatus and method for measuring a chemical/biological/nuclear agent in an environment which on the basis of a minimum of three measurements of the concentration of the vapor in the environment in question would predict, with a high degree of accuracy, (1) vapor dosage accumulated by users during the mission, (2) warns when the predicted dosages at a certain time point will exceed the myosis level, and (3) dewarns when the concentration is low enough that during the remainder of the mission, the users may avoid using protective clothing such as masks.

It is another object of the present invention to provide an apparatus for measuring concentrations based on Kalman filter predictions, where the parameters of the Kalman filter are adjusted periodically to improve accuracy of predictions.

It is a further object of the present invention to provide a simulated chemical detector and algorithm which is initialized with two initial concentration measurements to estimate a decay (or elevation) rate, as well as the level of chemical vapors in the environment and predicts subsequent measurement of concentration based on Kalman filtered estimates of the decay (or elevation) rate and of the level of chemical vapors in the environment. The algorithm constantly adjusts the Kalman filter parameters or attributes to minimize (or eliminate) the errors due to uncertainties in the system and errors of the measurements. In this manner, the algorithm predicts concentrations for a next subsequent measurement and the accumulated dosage by adding up the dosage for each time increment in order that the total dosage at the end of the mission time is predicted and may be compared with the predetermined harmful dosage level.

In accordance with the teachings of the present invention, an apparatus for measuring behavior parameters, specifically, concentrations of a chemical, biological, or nuclear agent in an environment comprises at least one, but preferably several detectors adapted to measure concentrations of the agent in the environment at predetermined times. A logic block in the algorithm of the present invention receives initial first and second concentration measures and estimates decay (or elevation) rate of the concentration of the agent in the environment.

It is important that a Kalman filter receives the estimated rate change of the concentration of the chemical, biological, and nuclear agent in the environment and, based on these estimates, predicts the next measurement concentration of the agent in the environment.

Detectors then make a next (third) measurement of the concentration of the agent in the environment. The measured concentration and the predicted concentration are compared in order to determine discrepancies therebetween which characterize errors in the system which due to changes in environmental parameters and measurement errors.

Using the magnitude of the discrepancy between the estimated and the measured concentrations, the algorithm further adjusts the Kalman filter parameters or attributes, to increase accuracy of the further predictions of the agent behavior in the environment. The predicted next concentrations are cumulatively added to obtain an accumulated dosage. The algorithm additionally predicts the total dosage at the end of the mission time period.

Warning/dewarning techniques are also included in the simulation. The effects of providing a gas mask to the user is simulated by the algorithm. The total dosage to the user is estimated by accumulating the concentration between the times when a gas mask is removed and being used. Likewise, the effects of removing the gas mask are estimated by accumulating the concentrations after removal of the mask with total accumulated dosages are compared to the myosis dosage level.

The subject invention provides a method of measurement of concentration of a chemical, biological, or nuclear agent including the steps of:

- providing an environment represented by a plurality of environment parameters;
- measuring first, second and third concentrations of the agent in sequence;
- predicting by means of a Kalman filter a predicted concentration of the agent corresponding to the third measurement (the prediction being made based on the first and second concentrations); and
- comparing the predicted concentration and the third measured concentrations and calculating system errors causing discrepancies between the predicted and measured concentrations.

Based on the calculated errors, the Kalman filter parameters are adjusted in order to optimize further predictions.

These and other novel features and advantages of this invention will be fully understood from the following detailed description and the accompanying Drawings.

BRIEF DESCRIPTION OF THE DRAWINGS

FIG. 1 is a simplified block diagram of a detector of the present invention;

FIG. 2 is a schematic representation of a Kalman filter loop;

FIG. 3 is a flow chart of a simulated Kalman filter mechanism;

FIGS. 4A and 4B show a flow chart of the simulated detector of the present invention including warning and dewarning logical blocks thereof;

FIG. 5 is a diagram showing the behavior of the predicted value for dosage AFF and the calculated dosage D based on the measured values of concentration over a mission duration;

FIG. 6 is a diagram showing the behavior of mean error of the concentration, MER, system error ER, and error variance PB during the mission duration;

FIG. 7 is a diagram showing the behavior of variance of the error ERVAR during the time of the mission;

FIG. 8 is a diagram showing the behavior of the Kalman filter gain, W, during the time of the mission;

FIG. 9 is a diagram showing the levels of the dosage with and without the gas mask during the mission; and FIG. 10 is a diagram showing the levels of the dosage with and without use of a gas mask during the mission and comparison to the detoxification level.

DETAILED DESCRIPTION OF THE PREFERRED EMBODIMENTS

Referring now to FIG. 1, there is schematically shown an apparatus 10 for measuring concentrations and accumulated dosages of a chemical, biological, or nuclear matter in an environment. Chemical detector 10 includes at least one, but preferably a plurality of detectors 11 (i.e., devices capable of detecting and measuring concentrations of a chemical vapor), algorithm 12 for processing the data received from the detectors 11, and processing means, such as computer 13 capable of running the algorithm 12.

In the chemical detector 10, measurements of vapor concentrations are periodically recorded. The algorithm 12 is initialized with the first two concentration measurements $Ct_1$ and $Ct_2$, which when received in the block 14 of the algorithm 12 are used to estimate the exponential decay (or elevation) rate and the level of the chemical vapors in the environment. Block 14 is a logic block which contains data representative of environment parameters, and therefore serves the function of the environmental model (to be discussed in detail in further paragraphs).

Based on the estimate of the decay (or elevation) rate of the chemical vapors in the environment output to the line 16, schematic logic block 17 simulates a Kalman filter, which predicts the next measurement of concentration of the chemical vapor in the environment and is output on the line 18.

The predicted next measurement of the concentration is received from the Kalman filter 17 to a comparing block 19. Simultaneously, a third measurement $Ct_3$ is taken by the detectors 11 and is supplied to the comparing block 19 through line 20 where it is compared with the predicted concentration supplied from the Kalman filter 17 through line 18.

The difference between the predicted concentration and the measured concentration $Ct_3$ is used to measure the errors in the algorithm's estimate of the environmental model. These errors may be due to uncertainties in the system and in the measurement technique.

The system error may be caused by system behavior that is not described by the exponential decay (or elevation), or by changes in the environment. Measurement errors may be caused by the electronics and detector technology. The detector concentration measurement error is a known quantity. The measurement error parameter values are used in the algorithm 12 to estimate the remaining system error parameter values. In block 19, algorithm 12 calculates the system error and Kalman filter's attributes or parameters and adjusts parameters of the Kalman filter 17 by means of supplying corresponding data to the Kalman filter 17 through the feedback line 21.

Once the Kalman filter's parameters are adjusted, the Kalman filter continues to predict concentrations for next measurements with a low noise signal. The predicted concentration values are then accumulated by adding up the dosage for each time period. The algorithm also predicts the total dosage at the end of a mission time period. The dosages predicted by the algorithm 12 (by means of the Kalman filter 17) are supplied to block 22 through the line 23. Simultaneously, block 22 receives data corresponding to a myosis level (or any other threshold level) which is compared with the dosage data received by block 22 through line 23. The results of the comparison between the predicted accumulated dosage of the chemical agent and the myosis level are supplied through line 24 to block 25, which is a warning/dewarning block actuated either when a predicted accumulated dosage reaches the myosis dosage level or when the algorithm 12 considers the accumulated dosage insufficient to harm a living organism in the environment containing the chemical, biological, or nuclear matter.

Although the detector panel of the present invention may function with a single detector 11, it is preferred that a series of detectors 11 would be positioned at several locations within the environment of interest, such as for example an aircraft enclosure or a chemical cloud, etc. Having several detectors 11 in a chemical cloud, aids in obtaining such important environmental parameters such as wind direction and wind velocity, crosswind standard deviation, variation in vertical direction, etc. It is then possible to predict the spread rate of the cloud, its arrival rate, as well as variability of the cloud as a function of distance from the center of the cloud. A set of several measurements from several detectors 11 will generally improve the overall accuracy of estimation of what is dynamically transpiring in the environment.

To demonstrate how the chemical detector 10 based on the algorithm 12 operates, a simulated model of an environment, a detector with measurement error, prediction equation, filtering to remove error and improve the prediction of the dosage at the end of the mission, a warning technique and a dewarning technique have been simulated, as will be described in further paragraphs in conjunction with FIGS. 2–4B. In describing the simulation, useful variables are defined as follows:

PR=predicted air exchange rate in the environment.
APR=average predicted environments air exchange rate.
PA=predicted level (amplitude) of the chemical in the environment.
APA=average predicted amplitude of the chemical in the environments.
PC=predicted concentration based upon the predicted air exchange rate and the predicted level of chemical in the environment.
FF=final predicted value of dosage at the end of the mission.
AFF=average of the final predicted value.
PB=system's error covariance.
PC-C=error between the predicted and the measured concentration.
ERVAR=mean error of the concentration, MER, and the variance of the error.
D=calculated dosage based on the measured values of concentration. The initial values of these variables are set at time equal to zero.

Figure 1:
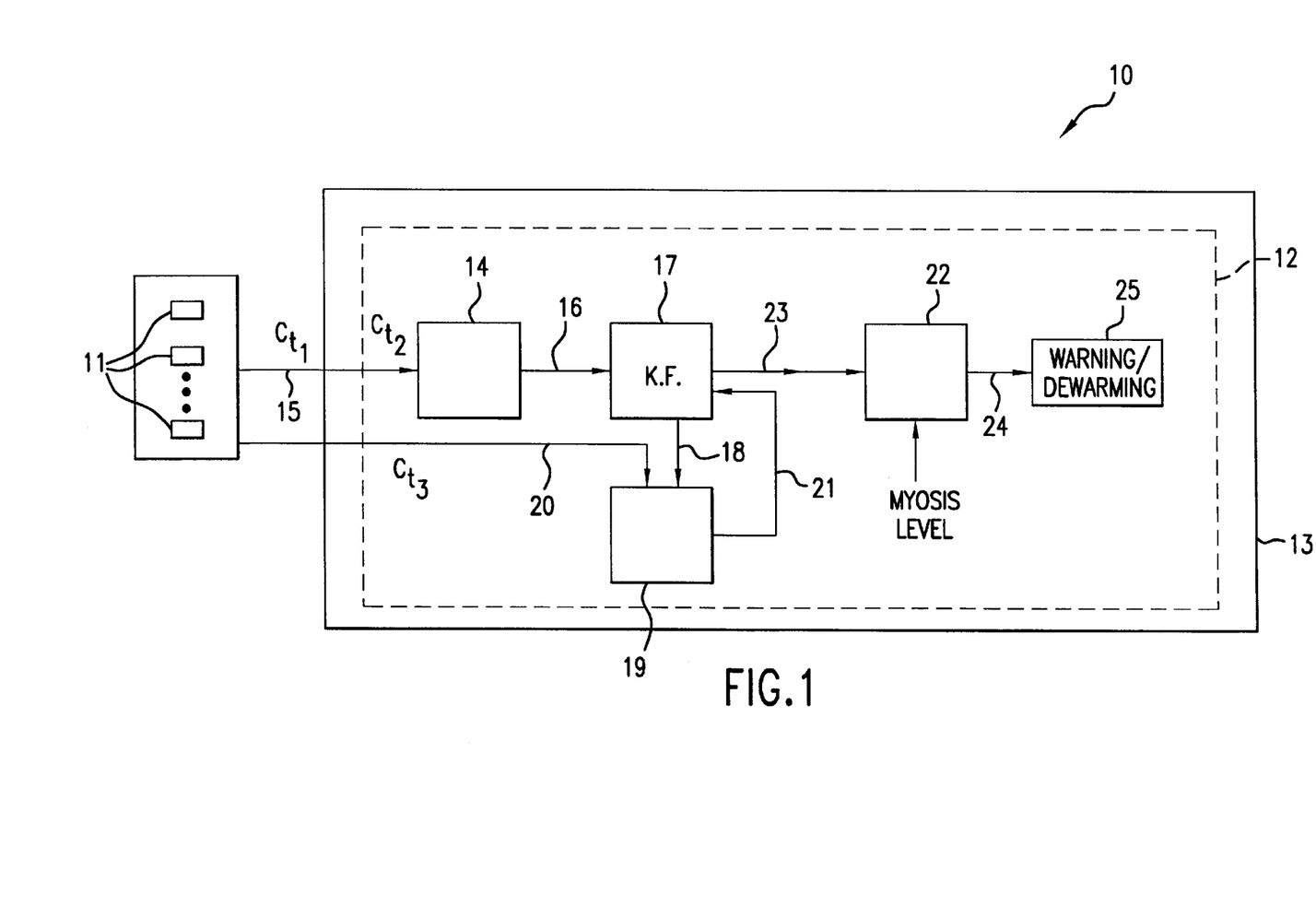
Figure 2:
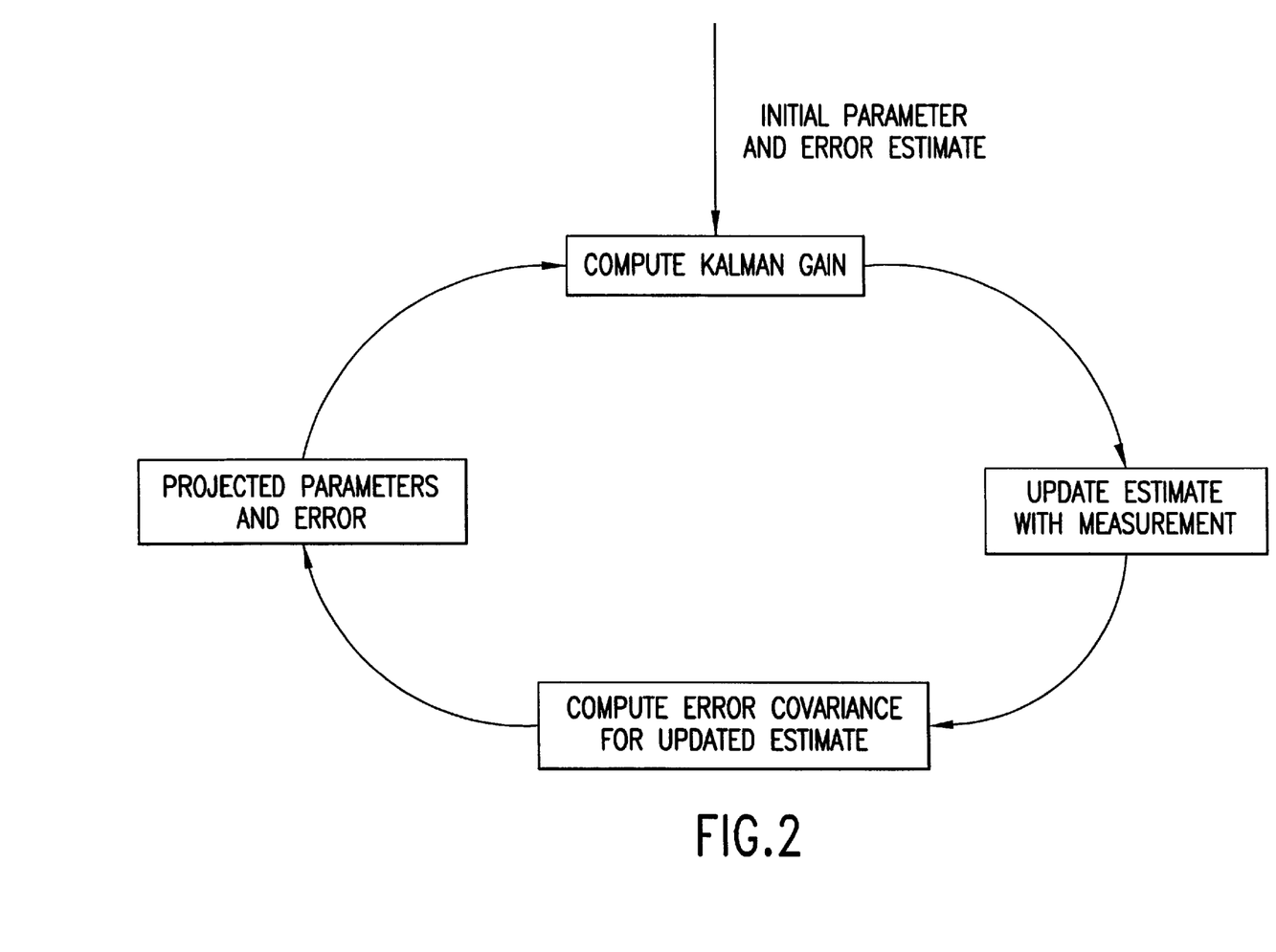

An essential portion of the algorithm of the present invention is use of the Kalman filter. The discrete Kalman filter is an iterative procedure containing several elements which are illustrated in FIG. 2. The filter is supplied with initial information, including the measurement error covariance, and estimates of the initial parameters and associated error. This information is used to calculate a filter gain matrix. The error between the parameter estimates and the measured data is determined and multiplied by the filter gain matrix to update the parameter estimate and estimated error.

The updated error and parameters are used as input to a model of behavior to predict the projected error and parameters at the next time instance. Initially when the model parameters are only rough estimates, the filter gain matrix insures that the measurement data is highly influential in estimating the stated parameters. As confidence in the accuracy of the parameters grows with each iteration, the filter gain matrix values decrease, causing the influence of the measurement data in updating the parameters and associated error to lessen. The concept of the Kalman filter is used in the detector 10 of the present invention for filtering to remove error and to improve the prediction of the accumulated dosage at a certain time instance and the total dosage at the end of the mission, as will be described in detail in further paragraphs.

Basically, in the chemical detector of the present invention, several measurements are taken and the algorithm calculates an estimate of the error in the measurement, calculates an estimate of the error in the environment, and then, using a Kalman filter and a Kalman filter gain, adjusts the filtering time constant as a function of the errors, for estimation of the decay rate of the environment. By calculating the decay (or elevation) rate in the environment, the device performs the next projected integrations of accumulated dosage over a predetermined period of time, and knowing the thresholds associated with accumulated dosage, warns or dewarns. In other words, the system advises whether it is safe to remove the protective mask based upon whether the predicted accumulated dosage is below the level which is hazardous to a user or another living organism in the chemical environment.

Conversely, if the measurement shows that there is no concentration of the chemical vapor in the environment, but the next measurement shows there is a sudden burst of chemicals within a given area, the algorithm of the present invention generates alarms and alerts the users within the chemical environment.

In the simulated model, an environment model has been built that represents the model of concentrations of chemicals in an aircraft. It is to be said that the environmental model indicative of both open and closed environment, such as aircraft, interiors of buildings and ships, or open fields is applicable in this invention as long as it is described by environmental parameters which are described by environment parameters following decaying (or elevating) exponentials of concentration of vapors in the modeled environment.

Figure 3:
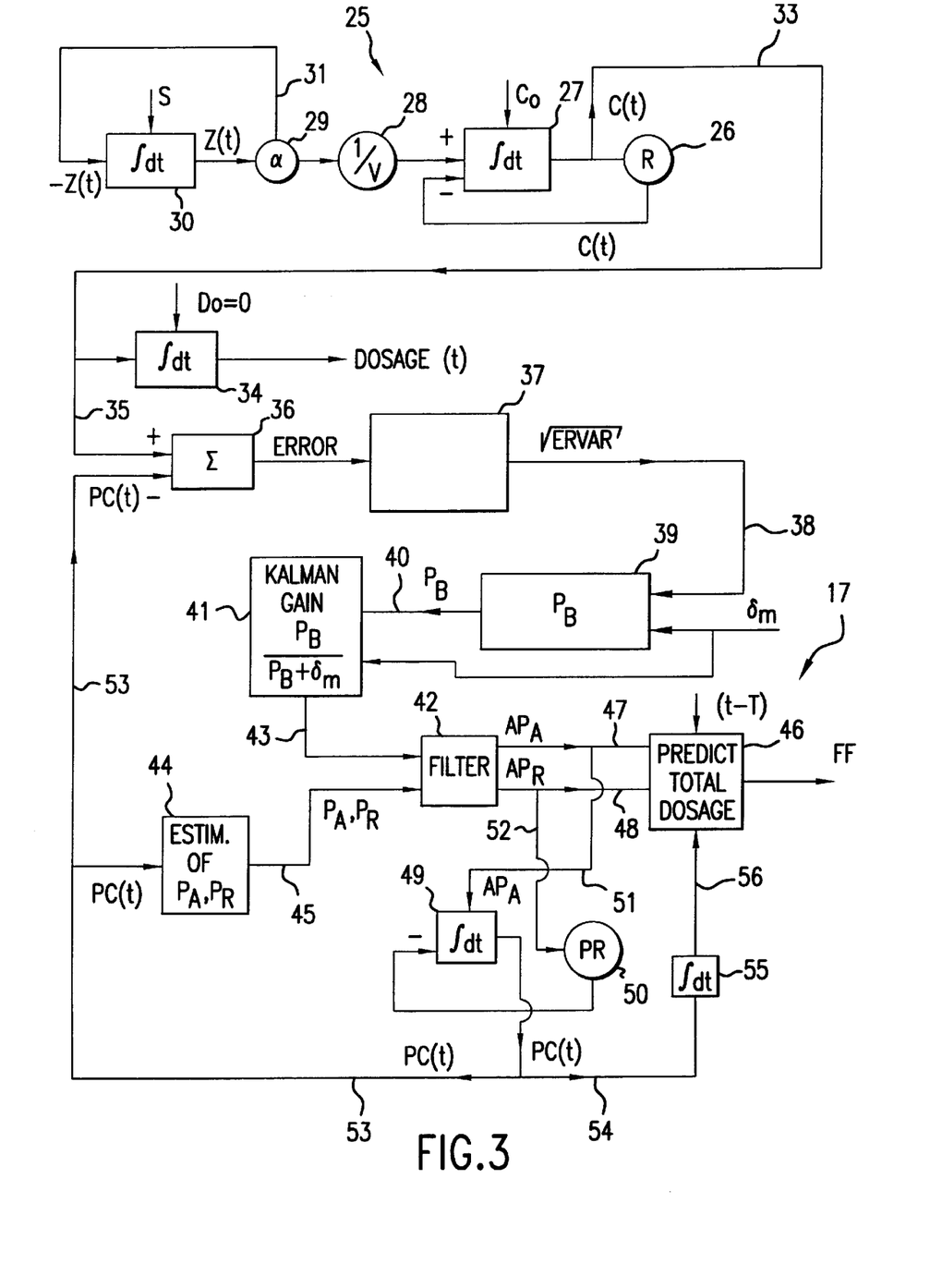

As shown in FIG. 3, the algorithm 12 includes a simulated environment model 25 which is represented by the blocks 26, 27, 28, 29, and 30. The flow chart is initiated in block 26 where the decay constants associated with the air exchange are set as described by the following equation:

$$R = \frac{-\ln(0.1)}{AT} \tag{1}$$

wherein: AT is air exchange time for example.

if AT=22,000 minutes, then R=0.1047

In block 28, the volume V of the environment is set.

In block 29, the evaporation rate $\alpha$ of a chemical in the environment is set as described by the following equation:

$$\alpha = \frac{-\ln(0.1)}{\tau} \qquad (2)$$

wherein: $\tau = TE \cdot 60$,

TE—evaporation time (in hours).
If evaporation time TE=1.5 hours, then
$\tau = TE \cdot 60 = 90$ minutes, and then
$\alpha = 0.02558$ In general, data on the evaporation rates and air exchange is based on observing the time to evaporate or exchange 90% of the original quantity of the chemical in the environment.

The evaporation rate $\alpha$ is supplied from block 29 over the line 31 to the block 30 to which the initial level S of the chemical in the liquid state is also applied. Block 30 monitors the evaporation of the chemical in the environment as a function of time and simulates the removal of liquid from the system as it evaporates as a function of time. In other words, the block 30 monitors what part of the chemical in liquid state is left in the system and constantly adjusts the evaporation rate $\alpha$ in the block 29 accordingly.

Data from the blocks 29, 28, and 26 are supplied to the block 27, to which the initial concentration $C_0$ of the agent is supplied wherein a concentration of the chemical C(t) as a function of time is calculated in accordance with the following equation:

$$C(t) := C_0 \cdot \exp(-R \cdot t) + \left(\alpha \cdot \frac{S}{V}\right) \left[\frac{(\exp(-\alpha \cdot t) - \exp(-R \cdot t))}{(R - \alpha)}\right] \qquad (3)$$

The simulated concentration C(t) is output by the block 27 onto the line 33 over which it is fed into the block 34 which integrates the concentration of the chemical in the environment over a certain period of time. Considering the initial dosage $D_0 = 0$, the output of block 34 is the cumulative dosage that would result from exposure to the chemical agent in the simulated environment during a predetermined period of time.

The simulated concentration C(t) is also fed through line 35 into summation block 36 which also receives a predicted concentration PC(t) to be compared with the simulated concentration C(t) received from the environmental model 25 (as will be described in detail in further paragraphs).

In the simulated environmental model, it is assumed that the duration of the mission is 720 minutes and that measurement of concentration is performed at a rate: one measurement every five minutes. The following equations set the time steps for the simulation.

$$MAXTIM = 720 \qquad MAXSTEPS = 144$$

$$DELTT = \frac{MAXTIM}{MAXSTEPS} \qquad DELTT = 5$$

$$I = 0, 1 \ldots MAXSTEPS$$

$$T_I = 1 + I \cdot \frac{MAXTIM}{MAXSTEPS}$$

$$T_{MAXSTEPS+1} = T_{MAXSTEPS} + \frac{MAXTIM}{MAXSTEPS}$$

In this simulation, it may be useful also to create logarithmic plots and graphs where it is important to have minimum values that are not zeros. For this reason, a variable called MIN has been introduced to be used where a small number is needed in the simulation:

$$MIN = 1 \cdot 10^{-10}.$$

In the environmental model, some normal random numbers were calculated which represent measurement errors. The concentration measurement error is assumed to be normally distributed with a mean of zero and a standard error of $$\mu_m = 0.0 \delta_m = 0.00015 \delta_M = 0.0001 \qquad (4)$$

The following equation calculates and stores 300 random numbers that represent measurement errors in the simulated environmental model.

$$J := 0, 1 \ldots 300 X_j := \mu m + \sigma m \sqrt{-2 \cdot \ln(md(1))} \cdot \cos(2 \cdot \pi \cdot md(1)) \qquad (5)$$

As described above, summation block 36 receives a simulated concentration C(t) and predicted concentration PC(t) and by subtracting the measured simulated concentration C(t) from the predicted simulation PC(t), block 36 calculates the total error as follows:

$$\text{error}(t) = PC(t) - C(t) \qquad (6)$$

The total error can be used to calculate the error variance $\sigma_e$ as follows:

$$\sqrt{ERVAR} = \sigma_e \approx \sqrt{\frac{(Error(t))^2}{n}} \qquad (7)$$

The error described by equation (6) is fed to the block 37 which performs the error estimation in accordance with the matrix $$\begin{bmatrix} APR_{I+1} \\ PA_{I+1} \\ PB_{I+1} \\ APA_{I+1} \\ PC_{I+1} \\ MER_{I+1} \\ ERVAR_{I+1} \end{bmatrix} := \begin{bmatrix} \text{if } \left[|PR_I| > |PR_0|, \left|APR_I + \frac{PB_I}{PB_I + \sigma m} \cdot (PR_I - APR_I)\right|, |PR_0|\right] \\ \text{if } \left[C_I > 6 \cdot \sigma m, \left|\frac{C_{I+1}}{\exp APR_I \cdot (T_I - T_{I+1})2} + \frac{C_I}{2}\right|, \frac{\sigma m}{2}\right] \\ \left|\left[1 - \left\{\frac{PB_I}{PB_I + \sigma m}\right\} \cdot PB_I + \sqrt{ERVAR_I - \sigma m^2}\right]\right| \\ \left|APA_I + \frac{PB_I}{PB_I + \sigma m} \cdot (PA_I - APA_I)\right| \\ \text{if } [|APR_I| > 0, APA_I \cdot \exp[-APR_I \cdot (T_{I+1} - T_I)] \cdot C_I, C_I] \\ MER_I + .1 \cdot [(C_I - PC_I) - MER_I] \\ ERVAR_I + .05 \cdot [[(C_I - PC_I) - MER_I]^2 - ERVAR_I] \end{bmatrix} \qquad (8)$$

The equation in the matrix 8 concerning the variable ERVAR$_{I+1}$ is calculated in block 37 and the result is output onto the line 38 through which the error estimation is fed to the block 39 which estimates the error covariance P$_B$ in accordance with the matrix 8 and also takes into consideration the concentration measurement errors σm described in previous paragraphs.

The error covariance P$_B$ is fed from block 39 through line 40 to filter gain block 41 in which the common filter gain W(t) is calculated in accordance with the following equations:

$$w(t) = \frac{P_B}{P_B + \sigma m} \quad (9)$$

$$P_B = \left[1 - \left(\frac{P_B}{P_B + \sigma m}\right)\right] \cdot P_B + \sqrt{\sigma_e^2 - \sigma_m^2} \quad (10)$$

where equation (10) corresponds to the equations in matrix (8). In block 41 the error covariance estimate P$_B$ and the measurement error on results in estimating the Kalman filter gain represented by the equation (9).

The estimated Kalman filter gain is then passed through the line 43 to the block 42 which calculates the predicted level (amplitude) P$_A$ of the chemical in the environment and the predicted error exchange rate P$_R$ in the environment. Block 42 serves for filtering data fed from the block 44 through line 45 in accordance with the Kalman filter gain w(t) supplied from block 41. In block 44, the predicted level of the chemical in the environment P$_A$ is calculated according to the matrix 8; and P$_R$ is calculated in accordance with the following equation:

$$PR_I = \left| \text{if} \left[ C_I > 6 \cdot \sigma m \left| \frac{\ln\left(\frac{C_{I+1}}{C_I}\right)}{T_{I+1} - T_I} \right| \cdot |PR_0| \right] \right| \quad (11)$$

wherein: $PR_0 = \frac{R}{8}$; and $\quad (12)$ $$C_I = \text{if} \left(|C_I| > \frac{\sigma m}{3}, |C_I|, \frac{\sigma m}{3}\right) \quad (13)$$

The data P$_A$ and P$_R$ are fed to the block 42 from the block 44 and filtered in the block 42 in accordance with the equations in matrix 8 to obtain the average predicted amplitude AP$_A$ of the chemical in the environment and the average predicted environment air exchange rate AP$_R$, which are then fed to the block 46 through the lines 47 and 48, respectively.

Prediction of Total Dosage block 46 calculates the dosage according to the following equation:

$$FF_I = \left[\frac{APA_I}{APR_I}(\exp(-APR_I \cdot T_I) - \exp(-APR_I \cdot T_{MAXSIEPS}))\right] + D_I \quad (14)$$

which is the predicted value for the dosage without mask protection.

Data from the lines 47 and 48 are also fed to blocks 49 and 50 through lines 51 and 52, in order to calculate a predicted concentration PC(t).

The predicted concentration PC(t) received on the output of the block 49 is supplied through the line 53 to the block 36 for comparison with the simulated concentration C(t) (as has been described in previous paragraphs) and to the block 44 for generating estimated P$_A$ and P$_R$.

The predicted concentration PC(t) is also supplied through line 54 to the block 55 which integrates predicted concentration over time and filters and smooths the predicted value for dosage according to the following equation:

AFF$_0$:=DOGB/2

AFF$_{I+1}$:=if [|D$_I$|≧AFF$_I$|, FF$_I$, [AFF$_I$−(FF$_I$−AFF$_I$)¼] $\quad (15)$ Thus calculated, the predicted dosage of the chemical is further supplied through line 56 to block 46 for predicting the total dosage.

The myosis level is the dosage that a human can inhale before impairment of vision occurs. For GB chemical, the dosage level is 0.05 mg/m$^3$. This dosage spread over a 720 minute period, is the level COGB. Below this level of concentration, there is no threat to humans, since they cannot accumulate a dosage in 720 minutes that will effect their performance.

$$COGB = \frac{DOGB}{720} \tag{16}$$

In order to plot the values of the concentration, an array of concentration plus measurement errors as a function of time was generated in the model.

In the detector simulation, it was assumed that the detector measures chemical vapor concentration $C_I$ with some error $X_J$ in the measurement time, $T_2$.

$$C_I := C(T_1) + X_J \tag{17}$$

Since the arrays of values within the simulation use the "Ith" and the "Ith plus one" values of the array $C(T_I)$ another value is added to the end of the array.

$$C_{MAXSIEPS+1} = C_{MAXSIEPS} \tag{18}$$

Since concentrations cannot be lower than zero in any real measurement instrument, the values of concentration are constrained to be greater than zero. Likewise for real instruments, any measurement of concentration are prevented from being smaller than ⅓ of the measurement error, in accordance with the following equation:

$$C_I := \text{if } \left( |C_I| > \frac{\sigma m}{3}, |C_I|, \frac{\sigma m}{3} \right) \tag{19}$$

("If" statements in this document are read using the format of if [logical test, then equation, else equation]. In the logical test, a "+" sign is read as a logical "OR" and a "·" is read as a logical "AND").

Also, the initial values of the variables are defined as follows:

$$PR_0 := \frac{R}{8} \quad APR_0 := \frac{R}{4} \quad PA_0 := \text{MIN} \quad APA_0 := \text{MIN} \tag{20}$$

$$PC_0 := \text{MIN} \quad MER_0 := 3 \cdot \sigma m \quad ERVAR_0 := \sigma m^2$$

$$D_0 := \text{MIN}$$

A variable PB (the system's error covariance) with an initial value of equal to σm:

$$PB_0 := \sigma m \tag{21}$$

In the detector algorithm simulation, the equations are defined that predict the air exchange rate from the measured values of concentration.

$$PR_I := \left| \text{if} \left[ C_I > 6 \cdot \sigma m, \left| \frac{-\ln\left(\frac{C_{I+1}}{C_I}\right)}{T_{I+1} - T_I} \right| \cdot |PR_0| \right] \right| \quad (22)$$

The measured dosage array is then given by the following equation:

$$D_{I+1} := D_I + \frac{C_I + C_{I+1}}{2} \cdot (T_{I+1} - T_I) \quad (23)$$

The arrays for APR, PA, APA, PC, MER, ERVAR, PB are solved simultaneously. The matrix (8) forces the solution of the equations on the right side of the matrix and uses previous values of the variables to calculate the left side of the equations.

When the Kalman filter gain is near unity the filtering of APA from PA and APR from PR does not occur, and the model uses the current values of PA and PR as the best estimates of the environment. It can be shown that the Kalman filter gain is near unity until the concentration becomes small and approaches the measurement error. Then the Kalman filter improves the predictions and stabilizes the prediction in the presence of the large errors.

Figure 4A:
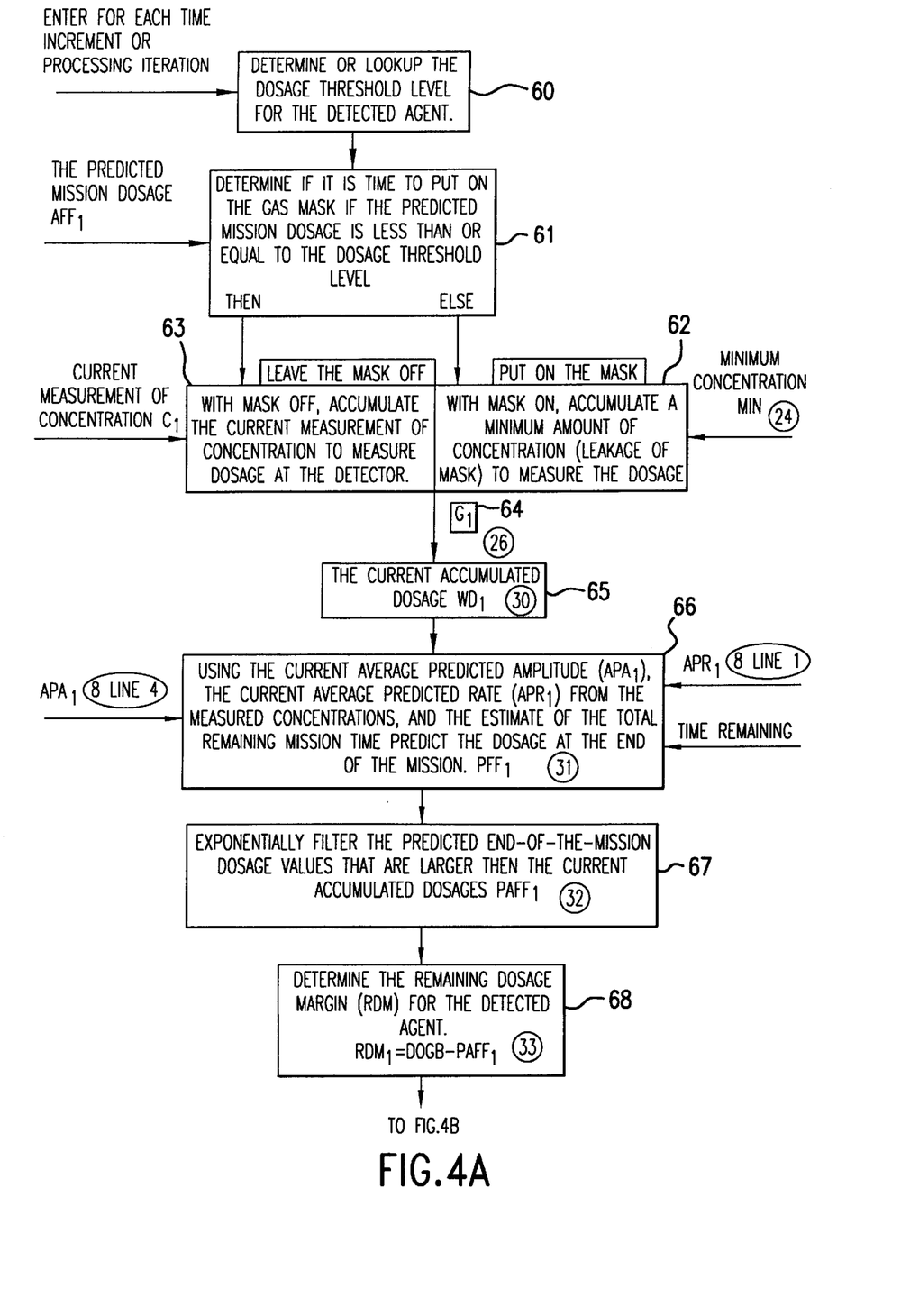
Figure 4B:
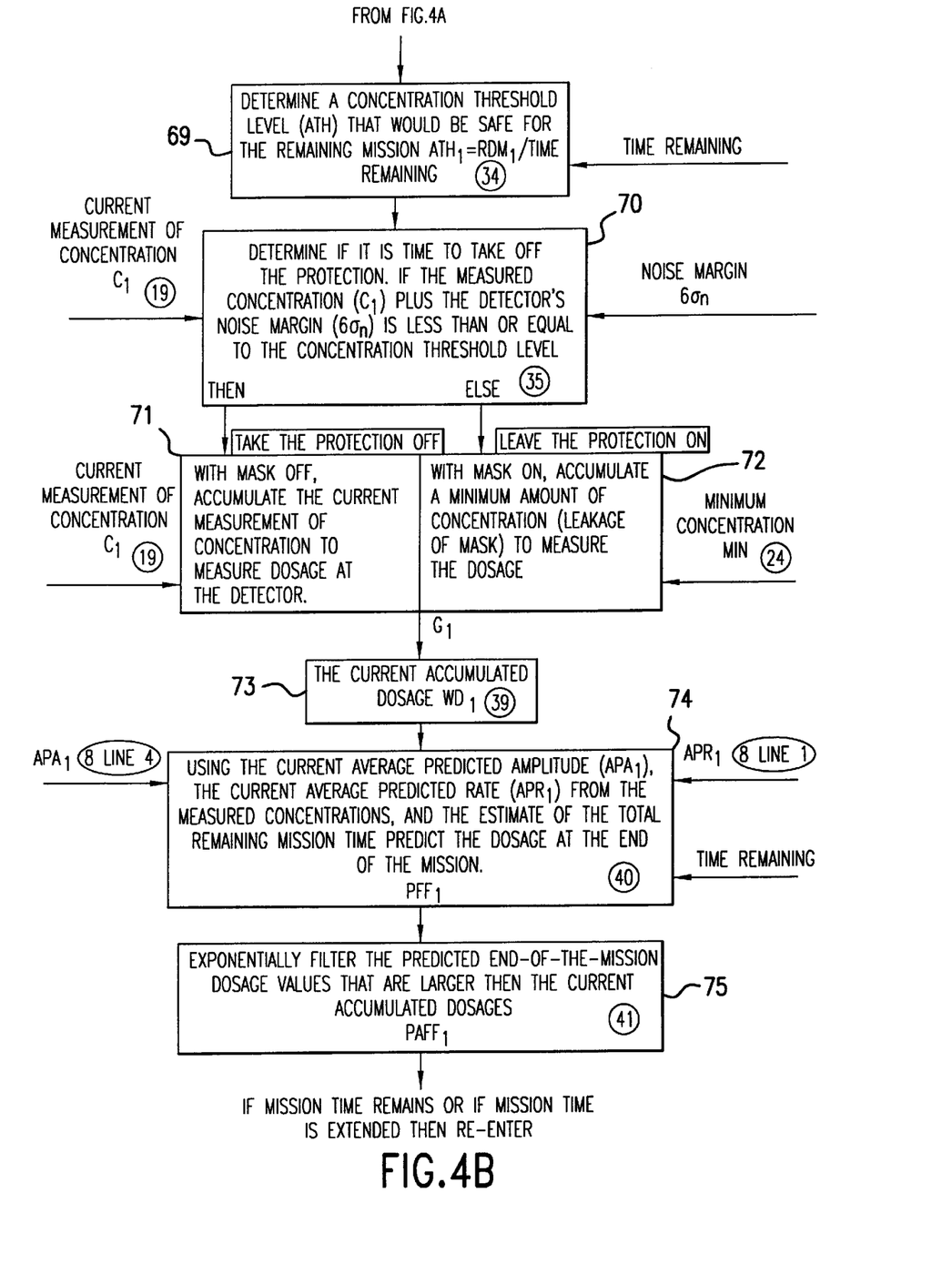
Figure 5:
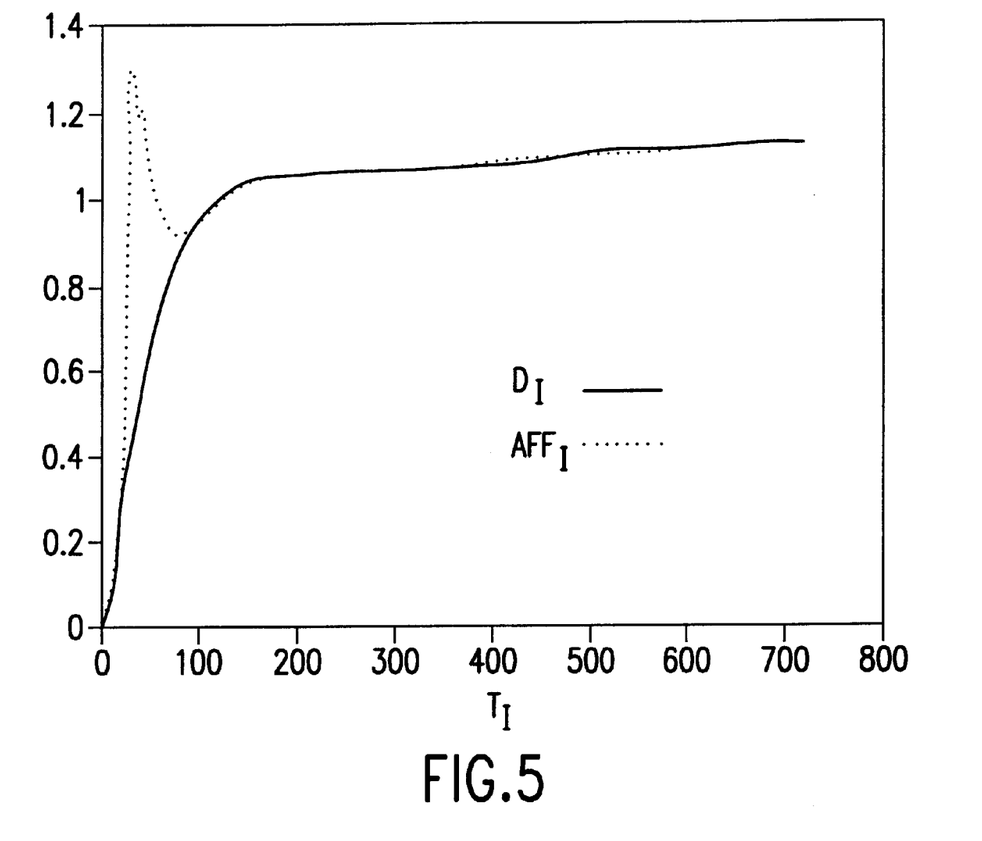
Figure 6:
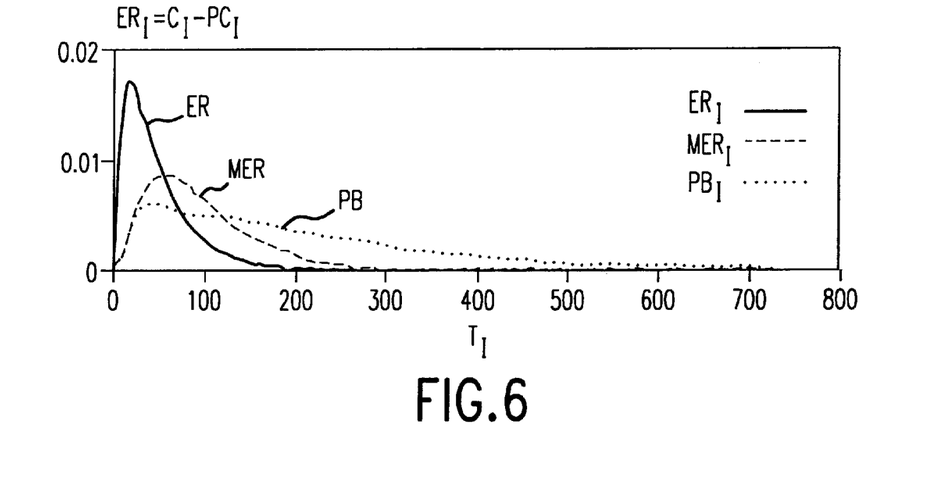
Figure 7:
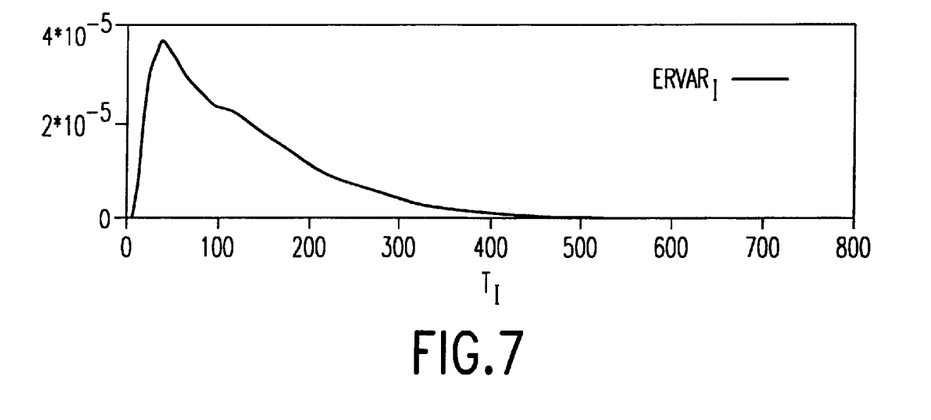
Figure 8:
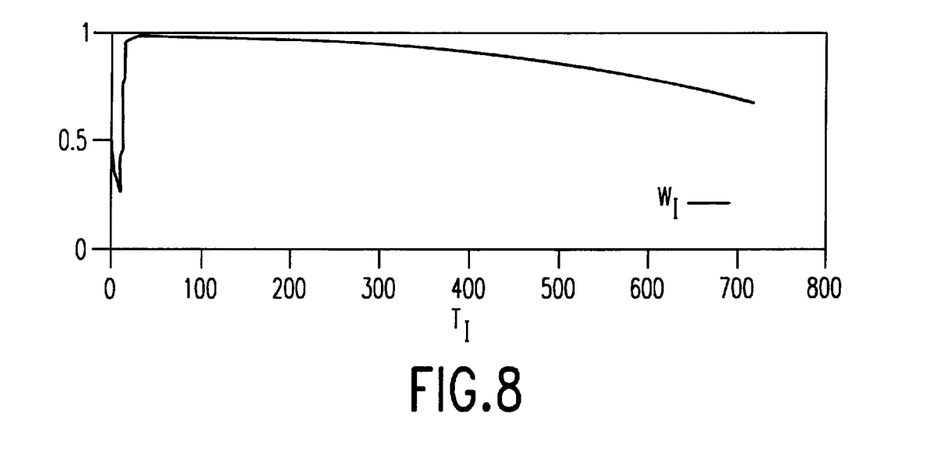

It is now possible to combine a simulation of protection with the prediction process described in previous paragraphs, to examine the effects of protection on user dosage levels, as shown in FIGS. 4A and 4B.

The flow chart initiates with the block 60 which is fed with the each time increment or processing iteration in accordance with the following equation:

$$MAXTIM = 720 \qquad MAXSTEPS = 144$$
$$DELTT = \frac{MAXTIM}{MAXSTEPS} \qquad DELTT = 5$$
$$I = 0, 1 \ldots MAXSTEPS$$
$$T_I = 1 + I \cdot \frac{MAXTIM}{MAXSTEPS}$$
$$T_{MAXSTEPS+1} = T_{MAXSTEPS} + \frac{MAXTIM}{MAXSTEPS}$$

In block 60, the dosage threshold level for a detected agent is determined or obtained from a look up table.

The logic further flows to block 61, to which the predicted mission dosage AFF calculated in accordance with the equation (15) is supplied. Block 61 determines if it is time to initiate protective measures such as putting on the gas mask.

If a gas mask is used, it is expected to protect an individual exposed to the chemical agent and to prevent the concentration of vapors above some minimum concentration level. This minimum level is as follows:

$$MIN = 1 \cdot 10^{-10} \quad (24)$$

It is further assumed that the individual uses some operating rules to determine when to put the gas mask on. If the detector with the Kalman filter predicts the total mission dosage AFF is greater than the myosis dosage level, DOGB (defined in the block 61), then the user puts the mask on and the logic flows to block 62.

If, however, the block 61 determines that the predicted mission dosage AFF is less than the dosage threshold level, then the logic flows to block 63 "mask off".

Block 62 is fed with the minimum concentration specified in the equation (24) while the block 63 is fed with the current measurement of concentration $C_I$ calculated in accordance with the following equation (25).

The values of concentration presented in the environment are defined as $V_I$, where the following equation gives the values of v as a function of the sample times, $T_I$.

$$V_I := C_I := C_0 \cdot \exp(-R \cdot T_I) + \left(\alpha \cdot \frac{S}{V}\right) \cdot \left[\frac{(\exp(-\alpha \cdot T_I) - \exp(-R \cdot T_I))}{(R - \alpha)}\right] \quad (25)$$

In block 63, the logic accumulates the current measurements of concentrations to measure the dosage (with the mask off).

In the block 62, the logic accumulates a minimum amount of concentration (leakage of the gas mask) to measure the dosage.

Data further flows to the block 64 in which the concentrations that the user is exposed to is determined by the following equation:

$$G_I := \text{if } [(AFF_I \leq DOGB), C_I, MIN] \quad (26)$$

From block 64, the flow-chart passes to block 65 in which the current accumulated dosage WD, is determined, as described in the following paragraphs.

Since the arrays of values within the simulation use the "Ith" and the "Ith plus one" values of the array $G_I$, another value is added to the end of the array.

$$G_{MAXSIEPS+1} := G_{MAXSIEPS} \quad (27)$$

The time when the mask is put on is determined by finding when the concentration is at a minimum. The following equation generates the set of indexes when the mask is on.

$$ON_I := \text{if}(G_I = MIN, I, O) \ ON_{MAXSIEPS+1} := ON_{MAXSIEPS} \ ON_{0'} := 2 \quad (28)$$

It is assumed that:
(a) the mask is always off at the start of the mission when the detector is initialized,
(b) that there is no accumulated dosage by the user and if warned,
(c) the user puts the mask on immediately,
(d) and that the accumulation of dosage stops when the user is warned. So the time when the user puts on the mask can be found by finding when $ON_I$ transitions from a "zero" to "I+1". The following equations determine the measurement step, OI, when the user puts the mask on.

$$ONS_I := \text{if}[[(ON_I) = 0] \cdot [(ON_{I+1}) = I+1], I, MAXSTEPS+1]$$

$$OI := \min(ONS)$$

$$OI = 4$$

$$T_{OI} = 20.1 \quad (29)$$

By modifying the equations that calculate the accumulated dosage based upon the exposure of the user, the block 65 calculates:

$$WD_0 := MIN \ WD_{I+1} := WD_I + G_I + G_{I+1}/2 \cdot (T_{I+1} - T_I) \quad (30)$$

$$WD_{MAXSIEPS} := WD_{MAXSIEPS-1}$$

From logic block 65, the data flows to block 66 which, using the current Average Predicted Amplitude (APA) calculated in the equation (8), line 4, the current Average Predicted Rate (APR) calculated in the equation (8), line 1, and the estimate of the total remaining mission time, predicts the dosage accumulated at the end of the mission PFF. The remaining mission time is the total mission minus the time of the measurement.

The predicted value for the dosage with protection is provided by the following equation:

$$PFF_I := \left[\frac{APA_I}{APR_I} \cdot (\exp(-APR_I \cdot T_I) - \exp(-APR_I \cdot T_{MAXSIEPS}))\right] + WD_I \quad (31)$$

From block 66, the logic moves to block 67 which exponentially filters the predicted end-of-the-mission dosage values by the following equation:

$$PAFF_0 := \frac{DOGB}{2} \quad (32)$$

$$PAFF_{I+1} :=$$

$$\text{if } \left[|WD_I| \geq |PAFF_I|, PFF_I, \left[PAFF_I + (PFF_I - PAFF_I) \cdot \frac{1}{4}\right]\right]$$

If the detector measures the concentration below a level that would not allow the accumulation of more than the myosis level, then the user may safely remove the gas mask.

From the block 67, the procedure flows to the block 68, in which the remaining dosage margin (RDM) for the detected agent is determined.

Defining a concentration level threshold below which the agent vapor will not present a hazard if integrated over the remaining duration of the mission, the remaining dosage margin is $$RDM_I := \text{if}[(DOGB-PAFF_I) > 0, DOGB-PAFF_I, MIN] \quad (33)$$

From the block 68, the data passes to the block 69 determining the safe concentration threshold level which is the remaining dosage margin divided by the remaining mission time.

$$ATH_I := \frac{RDM_I}{(T_{MAXSIEPS+1}) - T_I} + MIN \quad (34)$$

After the block 69, the logic flows to the block 70, where the exposure concentrations can be updated to match those when the mask is removed. Block 70 is fed with the current measurement of concentration (equation 19) and the detector is noise margin $\delta\delta_n$. Assuming the detector dewarns the user and the user removes the gas mask immediately, it must be insured that the values of the concentration are lower than ATH even with measurement error in the detector. Also, once the mask is removed, the detector should not switch back and forth between warn and dewarn. Block 70 uses the following logical statements: If the mask is on ($G_I$=MIN), then look for when the concentration (C) plus measurement noise is less than ATH; and once the mask is off, leave it off ($G_{I-1}=C_{I-1}$).

$$G_I := \text{if } [I<OI+2, G_I, \text{if } [[G_I=MIN) \cdot (C_I+6\sigma m<ATH_I)+(G_{I-1}=C_{I-1})],$$
$$C_I, MIN] \quad (35)$$

Further, the logic moves to the block 71 if the block 70 "allows" to "take protection off". Otherwise, the logic flows from the block 70 to the block 72 "leave the protection "on". Since the arrays of values within the simulation use the "Ith" and the "Ith plus one" values of the array $G_I$, another value is added to the end of the array.

$$G_{MAXSIEPS+1} := G_{MAXSIEPS} \quad (36)$$

The array of values that indicate when the mask is on is now updated.

$$ON_I := \text{if}(G_I=MIN, I, O) \; ON_{MAXSIEPS+1} := ON_{MAXSIEPS} \; ON_O := 2 \quad (37)$$

The time when the user takes off the mask is determined by finding when ONI transitions range from I to zero. The following equations determine the measurement step, OF, when the user takes the mask off.

$$ONE_I := \text{if } [(ON_{I-1}] \cdot [(ON_{I+1})=0], I, MAXSTEPS+1$$

$$OF := \min(ONE)$$

$$OF = 104 \quad (38)$$

From the blocks 71, 72, the logic moves to the block 73, which calculates the accumulated dosage based upon the exposure of the user when the gas mask is removed after the dewarning.

$$WD_0 := MIN$$

$$WD_{I+1} := WD_I + \frac{G_I + G_{I+1}}{2} \cdot (T_{I+1} - T_I)$$

$$WD_{MAXSIEPS} := WD_{MAXSIEPS-1} \quad (39)$$

Further, the procedure moves to the block 74, in which the predicted values for the dosage with protection PFF are updated in accordance with the following equation:

$$PFF_I := \left[\frac{APA_I}{APR_I}(\exp(-APR_I \cdot T_I) - \exp(-APR_I \cdot T_{MAXSIEPS}))\right] + WD_I \quad (40)$$

From the block 74, the logic flows to block 75, wherein the predicted value for the protected dosage is filtered by the following equation:

$$PAFF_0 := \frac{DOGB}{2} \quad (41)$$

$$PAFF_{I+1} :=$$

$$\text{if } \left[|WD_I| \geq |PAFF_I|, PFF_I, \left[PAFF_I + (PFF_I - PAFF) \cdot \frac{1}{4}\right]\right]$$

(41)

After block 75, if mission time remains or the mission time is extended, then the procedure is re-entered, starting again with the block 60.

Figure 9:
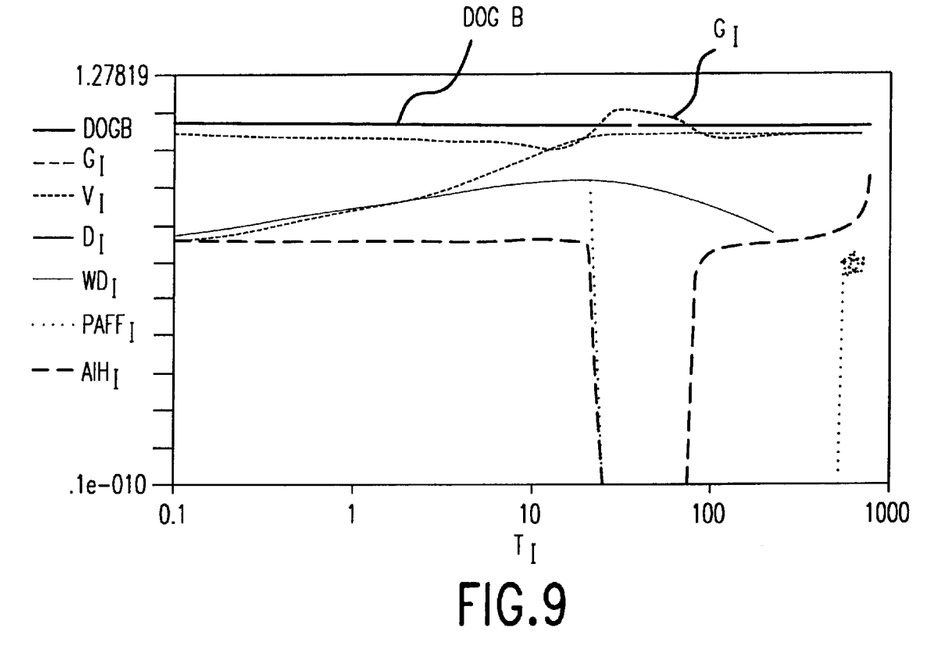

FIG. 9 shows the levels of dosage with and without the gas mask during the mission. In this FIG. 9, $$\max(v) = 0.01725 \qquad \max(WD) = 0.3272 \quad (42)$$

$$TOP_I := \text{if } (v_I < \max(v), 0, I) \quad \frac{\max(WD)}{DOGB} 100 = 65.439 \text{ Percent}$$

$$\max(TOP) = 4$$

The model of the present invention also simulates detoxidation effects. The user's body has the capabilities to detoxify some of the chemical. This capability is a function of the time the user has had to detoxify the chemical. This capability in some references is expressed as an increase in the myosis levels with exposure time. Thus, the exposure time of the user is important. This time is calculated by summing all of the times when the user does not have the gas mask on.

$$TT_0 := 1 \quad TT_{I+1} := TT_I + \text{if } (G_I > \text{MIN}, DELTT, 0.0) \quad (43)$$

$$TT_{MAXSIEPS} = 221$$

The myosis concentration divided by the mission times $TT_I$ is the myosis level spread over the $TT_I$ duration.

$$d_I := \frac{DOGB}{TT_I} \quad (44)$$

The myosis concentration level spread over the mission times with reported detoxification is as follows:

$$b_I := DOGB \cdot [0.827 \cdot [(TT_I)^{-0.826}]] \quad (45)$$

The largest of these two concentrations is given by the following equation:

$$e_I := \text{if } (d_I < b_I, b_I, d_I) \quad (46)$$

The myosis dosage level that includes detoxification capabilities is given by the following equation:

$$DMGB_I := (TT_I \cdot e_I) \quad (47)$$

Figure 10:
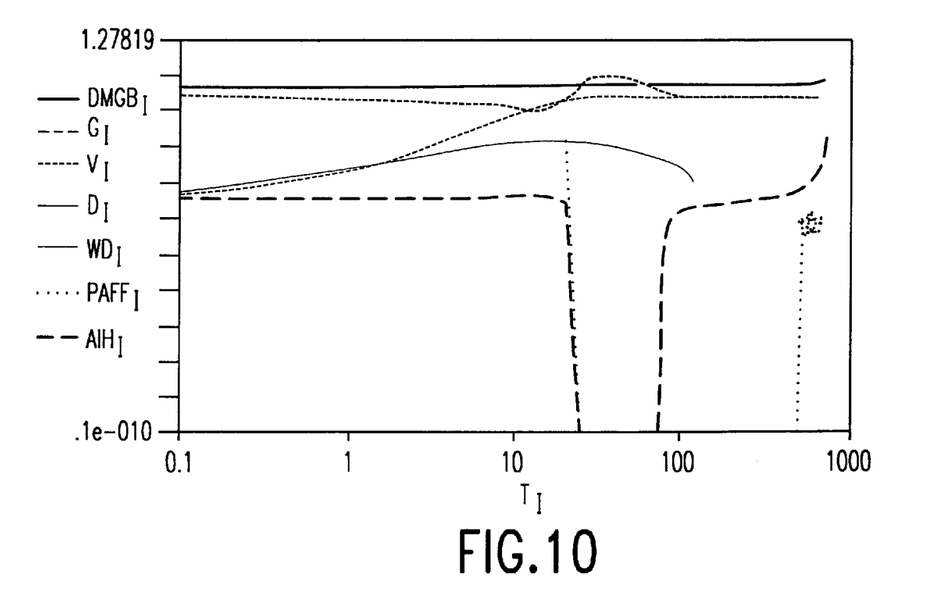

As shown in FIG. 10, the levels of dosages with and without the gas mask during the mission are compared to the detoxification levels. From FIG. 10, $$\max(v) = 0.001725 \qquad \max(WD) = 0.3272 \quad (48)$$

$$TOP_I := \text{if } (v_I < \max(v), 0, I) \quad \max(DMGB) = 1.0578$$

$$\max(TOP) = 4 \qquad \frac{\max(WD)}{\max(DMGB)} \cdot 100 = 30.9319 \text{ Percent}$$

FIGS. 5–8 show the behavior of the Kalman filter during the time of the mission. From these FIGS. 5–8, the following ranges were found to be stable: S from 0.45 to 45,000 60 from 00 to 4.0, α from 0.034 to 3.40, and R from 0.22 to 2,200.

As described, the detector of the present invention is built upon an algorithm that estimates decay and amplitude attributes or parameters of the chemical vapors in any environment;

estimates chemical vapor dosage accumulated by users in the environment;

predicts the chemical vapor dosage accumulated by the users at the end of a mission;

warns the users when the predicted dosage will exceed the myosis level;

and dewarns the user when the concentration is so low that for the remainder of the mission dosage levels will be less than the myosis level.

The model of the present invention can be used by civilians and military engineers to evaluate and analyze the following:

chemical detector's performance requirements;

chemical detector sensitivity and accuracy;

chemical detector algorithms;

performance of a dosage monitor and a concentration monitor;

automation of chemical detector warning and dewarning method;

and the detoxification of the chemical vapors.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described. Certain features may be used independently of other features, and in certain cases, particular locations of elements may be reversed or interposed, all without departing from the spirit or scope of the invention as described in the appended Claims.

What is claimed is:

1. An apparatus for measuring behavior of a chemical/biological/nuclear agent in an environment, comprising:
   (a) at least one detector adapted to measure concentration of said agent at predetermined time instances,
   (b) first means coupled to said at least one detector for estimating change rate of the concentration of said agent in said environment based on two consequent measurements of the concentration taken at time $t_1$ and time $t_2$, wherein $t_2 > t_1$,
   (c) a Kalman filter receiving said estimated change rate of the concentration for predicting the concentration of said chemical/biological/nuclear agent in said environment at time $t_3$, wherein $t_3 > t_2$,
   (d) second means having one input thereof coupled to said Kalman filter for receiving said predicted concentration corresponding to said time $t_3$, and further having another input for receiving a data corresponding to a concentration measured at said time $t_3$ by said at least one detector, said second means outputting data representative of an error causing discrepancy between said predicted concentration and said measured concentration measured at said time $t_3$, and
   (e) third means coupled between the output of said second means and the input at said Kalman filter for adjusting parameters of said Kalman filter, thereby increasing accuracy of prediction of said agent behavior in said environment.

2. The apparatus of claim 1, further comprising dosage prediction means coupled to the output of said Kalman filter for integrating a plurality of said predicted concentrations of said agent accumulated over a predetermined period of time.

3. The apparatus of claim 2, further comprising comparing means for comparing said predicted dosage accumulated over said predetermined period of time with a predetermined threshold dosage level.

4. The apparatus of claim 3, further including warning means actuated when said predicted dosage accumulated over said predetermined period of time approaches said threshold dosage level for indicating the need for initiating protective measures.

5. The apparatus of claim 4, further including dewarning means actuated when said predicted dosage accumulated over said predetermined period of time is below said threshold dosage level for indicating termination of protective measures.

6. The apparatus of claim 1, further including a plurality of said detectors.

7. The apparatus of claim 1, wherein said change rate of the concentration represents decay rate of said agent in said environment.

8. The apparatus of claim 1, wherein said change rate of the concentration represents rising rate of said agent in said environment.

9. The apparatus of claim 1, wherein said environment is represented by a plurality of environment parameters including: initial level of said agent, initial concentration of said agent, evaporation rate of said agent, air exchange rate in said environment, and duration of a mission.

10. The apparatus of claim 9, wherein said error output by said second means is determined by measurement errors inherent to said at least one detector and by deviations in at least one of said environmental parameters.

11. A method of measurement of concentration of a chemical/biological/nuclear agent, comprising the steps of:

(a) providing an environment represented by a plurality of environment parameters, (b) measuring first, second and third concentrations of said agent in sequence at a first time, a second time, and a third time, respectively, (c) providing a Kalman filter having Kalman filter parameters, (d) predicting, by means of said Kalman filter a predicted concentration of said agent corresponding to said third time, said prediction being made based on said first and second concentrations measured at said first and second times, (e) comparing said predicted concentration and said measured third concentration, (f) calculating system errors causing discrepancies between said predicted concentration and said measured third concentration, and (g) adjusting said Kalman filter parameters on the basis of said system errors, thus improving further predictions of concentrations by said Kalman filter.

12. The method of claim 11, further comprising the steps of:

providing at least one detector for measurement of said first, second and third concentrations of said agent in said environment.

13. The method of claim 12, further comprising the steps of:

providing a plurality of said detectors, and placing said detectors within said environment at predetermined locations.

14. The method of claim 11, further comprising the step of:

predicting a dosage of said agent accumulated over a predetermined time duration by integrating said predicted concentrations of said agent over said predetermined time duration.

15. The method of claim 14, further comprising the steps of comparing said predicted accumulated dosage of said agent with a predetermined dosage threshold.

16. The method of claim 15, further comprising the steps of:

actuating warning indicia when said predicted accumulated dosage reaches said predetermined dosage threshold.

17. The method of claim 15, further comprising the steps of:

actuating dewarning indicia when said predicted accumulated dosage falls below said predetermined dosage threshold.

* * * * *